United States Patent
Akamaru

(10) Patent No.: US 10,916,334 B2
(45) Date of Patent: Feb. 9, 2021

(54) SAMPLE ANALYSIS SYSTEM

(71) Applicant: Shimadzu Corporation, Kyoto (JP)

(72) Inventor: Hisamitsu Akamaru, Takatsuki (JP)

(73) Assignee: Shimadzu Corporation, Kyoto (JP)

(*) Notice: Subject to any disclaimer, the term of this patent is extended or adjusted under 35 U.S.C. 154(b) by 308 days.

(21) Appl. No.: 15/823,922

(22) Filed: Nov. 28, 2017

(65) Prior Publication Data

US 2018/0150616 A1    May 31, 2018

(30) Foreign Application Priority Data

Nov. 28, 2016 (JP) ................. 2016-229745

(51) Int. Cl.
*G01J 3/10* (2006.01)
*G01N 23/223* (2006.01)
(Continued)

(52) U.S. Cl.
CPC ............... *G16C 99/00* (2019.02); *G01J 3/108* (2013.01); *G01N 21/35* (2013.01); *G01N 23/223* (2013.01);
(Continued)

(58) Field of Classification Search
CPC ......... G16C 99/00; G16C 20/20; G01J 3/108; G01N 21/35; G01N 23/223; G01N 21/75
See application file for complete search history.

(56) References Cited

U.S. PATENT DOCUMENTS 5,130,559 A * 7/1992 Leifeld ............... D01G 31/003
                                                        19/65 A
2006/0029182 A1    2/2006 Tani et al.
(Continued)

FOREIGN PATENT DOCUMENTS

JP    H06-337252    12/1994
JP    H08-334481 A  12/1996
(Continued)

OTHER PUBLICATIONS

Extended European Search Report dated Jun. 11, 2018 for the corresponding European Patent Application No. 17203167.6.
(Continued)

*Primary Examiner* — Regis J Betsch
*Assistant Examiner* — Jeremy A Delozier
(74) *Attorney, Agent, or Firm* — Muir Patent Law, PLLC

(57) ABSTRACT

A sample analysis system is provided with: a reference substance database including measurement results and component classification information of reference substances obtained by each analysis device on information of each reference substance; a reference substance designation unit; a measurement result collation unit to obtain the commonality of the components, the difference between the physical quantities of the respective components, and the degree of coincidence of the measurement results for each analysis device for the designated reference substance; an integration coincidence degree calculation unit to obtain an integration degree of coincidence; and a judgment unit to judge whether or not the difference between the contents of contained components is within an allowable range and classify the corresponding component based on the component classification information.

5 Claims, 9 Drawing Sheets

(51) Int. Cl.
  *G01N 21/35* (2014.01)
  *G16C 99/00* (2019.01)
  *G01N 33/02* (2006.01)
  *G16C 20/20* (2019.01)
  *G01N 21/17* (2006.01)
  *G01N 21/75* (2006.01)

(52) U.S. Cl.
  CPC ............ *G01N 33/02* (2013.01); *G16C 20/20* (2019.02); *G01N 21/75* (2013.01); *G01N 2021/1734* (2013.01); *G01N 2021/3595* (2013.01); *G01N 2223/652* (2013.01)

(56) References Cited

U.S. PATENT DOCUMENTS

| | | | |
|---|---|---|---|
| 2006/0291619 A1 | 12/2006 | Statham | |
| 2012/0062873 A1 | 3/2012 | Stewart et al. | |
| 2012/0072122 A1* | 3/2012 | Schweitzer | G06F 16/2462 702/19 |
| 2013/0208850 A1* | 8/2013 | Schmitt | G01N 23/20 378/4 |
| 2014/0005980 A1* | 1/2014 | Green | G01N 24/08 702/181 |
| 2014/0088876 A1* | 3/2014 | Shiley | G01V 13/00 702/8 |
| 2016/0292197 A1 | 10/2016 | Morimoto et al. | |

FOREIGN PATENT DOCUMENTS

| | | |
|---|---|---|
| JP | 2000-258340 A | 9/2000 |
| JP | 2001-074650 | 3/2001 |
| JP | 2006-119108 A | 5/2006 |
| JP | 2007-003532 A | 1/2007 |
| JP | 2007-278746 A | 10/2007 |
| JP | 2010-223908 | 10/2010 |
| JP | 2010-249845 A | 11/2010 |
| JP | 2015-153296 A | 8/2015 |
| JP | 2016-121019 A | 7/2016 |
| JP | 2016-176817 A | 10/2016 |
| WO | 2011/103161 A2 | 8/2011 |
| WO | 2015/079535 A1 | 6/2015 |

OTHER PUBLICATIONS

Extended European Search Report dated Sep. 5, 2017 for the related European Patent Application No. 17165987.3.
Chinese first Office Action dated Jun. 26, 2018 for the related Chinese Patent Application No. 201710259756.1.
First Office Action dated Nov. 13, 2018 for related U.S. Appl. No. 15/484,529.
Office Action, issued from the Japanese Patent Office, dated Nov. 12, 2019, for corresponding Japanese Patent Application No. 2016-229745, with English-language machine translation thereof (6 pages).
First Office Action dated Sep. 17, 2019 for related Japanese Patent Application No. 2016-084964, submitted with a machine translation.

* cited by examiner

| No | Component | Content | Required | No influence |
|---|---|---|---|---|
| 1 | Ca | 9.3611 | ☑ | ☐ |
| 2 | Zn | 1.5266 | ☑ | ☐ |
| 3 | S | 0.9067 | ☑ | ☐ |
| 4 | Cl | 0.0396 | ☐ | ☐ |
| 5 | Si | 0.0247 | ☐ | ☐ |
| 6 | Sr | 0.0079 | ☐ | ☐ |
| 7 | C7H9N | 88.1334 | ☐ | ☑ |

FIG. 2

| No | Wave number (cm-1) | Absorption rate | Required | No influence |
|---|---|---|---|---|
| 1 | 711 | 0.50 | ☐ | ☑ |
| 2 | 872 | 0.70 | ☐ | ☐ |
| 3 | 917 | 0.40 | ☑ | ☐ |
| 4 | 964 | 0.70 | ☑ | ☐ |
| 5 | 1439 | 1.00 | ☑ | ☐ |
| 6 | 1536 | 0.25 | ☐ | ☐ |
| 7 | 2236 | 0.15 | ☑ | ☐ |
| 8 | 2847 | 0.15 | ☑ | ☐ |
| 9 | 2921 | 0.20 | ☑ | ☐ |

FIG. 3

| No | Reference substance name |
|---|---|
| 1 | Spring A |
| 2 | Spring B |
| 3 | Spring C |
| 4 | Bottom board A |
| 5 | Bottom board B |
| 6 | Bottom board C |
| 7 | Bottom board D |
| 8 | Resin panel A |
| 9 | Resin panel B |
| 10 | Resin panel C |
| 11 | Resin panel D |
| 12 | Resin panel E |
| 13 | Cord A |
| 14 | Cord B |
| 15 | Cord C |

Reference Substance List

View · Details · Analysis · Close

FIG. 7

Which analysis do you want to execute?

EDX · FTIR · Integration · Cancel

| No | Component | Bottom board B | Analysis target sample | Difference / content of bottom board B | Judgment result |
|---|---|---|---|---|---|
| 1 | Ca | 9.3611 | 6.8300 | -27.0% | Out of range |
| 2 | Zn | 1.5266 | 1.5101 | -1.1% | Within range |
| 3 | S | 0.9067 | 0.7823 | -13.7% | Within range |
| 4 | Cl | 0.0396 | 0.0400 | 1.0% | Within range |
| 5 | Si | 0.0247 | 0.0267 | 8.1% | Within range |
| 6 | Sr | 0.0079 | 0.0000 | -100.0% | Within range |
| 7 | C7H9N | 88.1334 | 90.8044 | 3.0% | Within range |
| 8 | Al | | 0.0065 | | Within range |

(b)

| No | Wave number (cm-1) | Bottom board B | Analysis target sample | Difference | Judgment Result |
|---|---|---|---|---|---|
| 1 | 711 | 0.50 | 0.48 | -0.02 | Within range |
| 2 | 872 | 0.70 | 0.97 | 0.27 | Out of range |
| 3 | 917 | 0.40 | 0.42 | 0.02 | Within range |
| 4 | 964 | 0.70 | 0.66 | -0.04 | Within range |
| 5 | 1439 | 1.00 | 1.00 | 0.00 | Within range |
| 6 | 1536 | 0.25 | 0.29 | 0.04 | Within range |
| 7 | 2236 | 0.15 | 0.15 | 0.00 | Within range |
| 8 | 2847 | 0.15 | 0.13 | -0.02 | Within range |
| 9 | 2921 | 0.20 | 0.21 | 0.01 | Within range |

FIG. 9B

| Analysis results | |
|---|---|
| Reference substance name | Bottom plate B |

| Measurement data | |
|---|---|
| EDX | Bottom plate B Lot 0001.edx |
| FTIR | Bottom plate B Lot·0001.ftir |

| | |
|---|---|
| Integration degree of coincidence | 0.72 |
| Additional information | Necessary component (Ca) is insufficient. Large amount of impurities (wave number 872 cm-1) are contained. |

FIG. 10

| Order | Reference substance | Integration coincidence degree | Necessary | No influence | Impurities |
|---|---|---|---|---|---|
| 1 | Reference substance _2 | 0.649 | Ca ↓ | 872cm-1 ↑ | |
| 2 | Reference substance _5 | 0.592 | | | Al |
| 3 | Reference substance _6 | 0.524 | Zn ↑ | 964cm-1 ↑ | |
| 4 | Reference substance _7 | 0.519 | Sr ↑ | | |
| 5 | Reference substance _10 | 0.498 | | | Hg |

FIG. 12

SAMPLE ANALYSIS SYSTEM

This application claims priority to Japanese Patent Application No. 2016-229745, filed Nov. 28, 2016, herein incorporated by reference in its entirety.

TECHNICAL FIELD

The present invention relates to a sample analysis system for analyzing a target sample by collating measurement data of the target sample obtained by using plural kinds of analysis devices with measurement data of a reference substance. The plural kinds of analysis devices include: at least one of a fluorescent X-ray analyzer, an atomic absorption spectrophotometer, and an inductively coupled plasma emission analyzer, which are suitable for analyzing an inorganic substance; and at least one of an infrared spectrophotometer and a Raman spectrophotometer, which are suitable for analyzing an organic substance.

BACKGROUND ART

If products, such as, e.g., foods, are shipped to a market in a state in which foreign substances, such as, e.g., vinyl pieces and metal pieces, are mixed, the reliability to the product will be significantly lowered. For this reason, a product contamination inspection is carried out at factories, etc. When a foreign substance is found by a product contamination inspection, the foreign substance is analyzed to determine contained substances, contained elements, their contents, etc., and identify the foreign substance by a reference substance database. Then, the source and/or the contamination route are figured out.

As an analysis device suitable for analyzing organic foreign substances such as vinyl pieces, there exists a Fourier transform infrared spectrophotometer (FTIR). In the FTIR, an interference wave generated by a Michelson type interferometer equipped with a fixed mirror and a moving mirror is irradiated to a foreign substance, and the transmitted light and the reflected light are measured as an interferogram. This is Fourier-transformed to thereby obtain an absorption spectrum in which the wave number is shown on the horizontal axis and the intensity (absorbance, transmittance, etc.) is shown on the vertical axis. In the absorption spectrum, peaks corresponding to contents of substances appear at wave numbers (wavelengths) corresponding to the vibration energy or the rotational energy of various substances contained in a foreign substance. Therefore, the positions (the wave number) and the magnitudes (absorption rates) of the absorption peaks are obtained from the absorption spectrum of the foreign substance as measurement results and compared with the measurement results of various reference substances preliminarily stored in a reference substance database. With this, the degree of coincidence of an organic substance contained in the foreign substance and the reference substance can be obtained (see, for example, Japanese Unexamined Patent Application Publication No. 2001-74650, herein incorporated by reference in its entirety).

On the other hand, as an analysis device suitable for analyzing foreign substances including inorganic substances such as metal fragments, there exists an energy dispersive fluorescent X-ray analyzer (EDX). In the EDX, an X-ray is irradiated on a foreign substance to acquire the spectrum of the fluorescent X-ray. In the fluorescent X-ray spectrum, peaks of the fluorescent X-ray appear at the energy positions unique to each element. Therefore, by examining the peak positions of the fluorescent X-ray spectrum, it is possible to identify the elements contained in the foreign substance. A quantitative method of the specified element includes two methods: an FP method (fundamental parameter method) and a calibration curve method. In the FP method, a quantitative value of each element is obtained as a measurement result by reproducing the measured intensity of the fluorescent X-ray using the theoretical formula, assuming the composition of the main component (see, for example, Japanese Unexamined Patent Application Publication No. 6-337252 and Unexamined Patent Application Publication No. 2010-223908, each of which is herein incorporated by reference in their entirety). In the calibration curve method, it is necessary to create calibration curves by measuring a plurality of standard samples of the same composition in which the content is known. On the other hand, in the FP method, there is no need to do it, so there is an advantage that an analysis can be easily performed. The quantitative value by the FP method is also called a semi-quantitative value to distinguish it from the exact quantitative value obtained by the calibration curve method. By comparing the semi-quantitative value (measurement result) of each element of the foreign substance obtained by the FP method with the semi-quantitative value (measurement result) of each element contained in various reference substances preliminarily stored in the reference substance database, the degree of coincidence of the inorganic substance contained in foreign substance and that contained in the reference substance can be obtained.

SUMMARY OF THE INVENTION

Conventionally, for a foreign substance including both an inorganic substance and an organic substance, the degree of coincidence was obtained by comparing the measurement result (the absorption spectrum or the peak position and the absorption rate in the absorption spectrum) acquired using an FTIR with the measurement result stored in a reference substance database, and further the degree of coincidence was also obtained by comparing the measurement result (semi-quantitative result) acquired using an EDX with the measurement result stored in a reference substance database. In the FTIR, the degree of coincidence with the reference substance of an organic substance is mainly obtained, and in the EDX, the degree of coincidence with the reference substance of an inorganic substance is mainly obtained. For this reason, there was a case in which the result obtained from the FTIR measurement result and the result obtained from the EDX measurement result did not match. In such a case, a foreign substance cannot be specified from the degree of coincidence of the measurement results. This requires the user to identify the foreign substance by confirming respective measurement results on both devices, and the judgment is left to the experience of the user. For this reason, depending on the skill level of the user, there is a problem that the same foreign substance may be specified as different substances (for example, even if a user has sufficient knowledge on inorganic substances, the user may erroneously judge the specific result of the FTIR if the knowledge about organic substances is not sufficient).

In order to solve these problems, in the earlier application (Japanese Patent Application No. 2016-084964, herein incorporated by reference in its entirety), the applicant of the present invention proposed a sample analysis system in which a measurement result (absorption spectrum or the peak position and the absorption rate in the absorption spectrum) of an analysis target sample acquired using an FTIR and a measurement result (semi-quantitative result) obtained from a fluorescence spectrum obtained using an EDX are compared with respective measurement results of the reference substance to obtain the degree of coincidence; for each reference substance, an integration degree of coincidence is obtained by integrating the degrees of coincidence; and a list of a predetermined number of reference substances in descending order of the integration degree of coincidence is output. According to this sample analysis system (hereinafter referred to as "sample analysis system of the prior application"), in addition to specifying foreign substances described in relation to the prior art, it can be used for analyzing various analysis target samples such as product inspection, etc. This enables an easy identification of the reference substance closest to the analysis target sample irrespective of the skill of the user.

However, depending on a sample, for example, in cases where an analysis target sample contains a number of impurities, in some cases, only reference substances with low integration degree of coincidence are listed in the output list. In this case, it cannot be judged only by the value of the presented integration degree of coincidence, and the user must carefully examine the measurement result of the analysis target sample and the measurement result of the reference substance. This was a burden for a less skilled user. Embodiments of the present invention improve the sample analysis system of the prior application on this point and may solve one or more of the aforementioned problems.

Although a combination of an FTIR and an EDX is exemplified as specific analysis devices here, an atomic absorption spectrophotometer or an inductively coupled plasma emission analyzer is sometimes used as a device suitable for analyzing an inorganic substance. In addition, a Raman spectrophotometer is sometimes used as a device suitable for analyzing an organic substance. Further, in some cases, three or more devices are used in combination to analyze a foreign substance and the like. In any of these cases, there was the same problem as described above.

According to the present invention made by considering the aforementioned problems, a sample analysis system used for analyzing an analysis target sample from a measurement result of a component contained in the analysis target sample and a physical quantity corresponding to a content of the component obtained by a measurement by each of a plurality of analysis devices including at least one of a fluorescent X-ray analyzer, an atomic absorption spectrophotometer, and an inductively coupled plasma emission analyzer and at least one of an infrared spectrophotometer and a Raman spectrophotometer, includes:

a) a reference substance database in which information on a plurality of reference substances is accumulated, wherein the information on each reference substance includes measurement results of a plurality of components and their physical quantities included in the reference substances and measured by each of the plurality of analysis devices and component classification information indicating whether or not each of the plurality of components characterizes the reference substance;

b) a reference substance designation unit configured to allow a user to designate one or more reference substances to be collated with the analysis target sample from among the plurality of reference substances;

c) a measurement result collation unit configured to, for each of the one or more reference substances and for each analysis device, collate the measurement result of the reference substance with the measurement result of the analysis target sample, and obtain a commonality of components indicating whether or not a common component exists, a difference between the physical quantities of respective components, and a degree of coincidence of the measurement result;

d) an integration coincidence degree calculation unit configured to obtain an integration degree of coincidence in which the degrees of coincidence obtained for respective analysis devices are integrated for each of the one or more reference substances, e) a judgment unit configured to, for each of the one or more reference substances, judge whether or not a difference between the physical quantities of the components included in the reference substance is within a predetermined allowable range and classify a component in which a difference of the physical quantity is outside the allowable range a component whose difference of the physical quantity is outside the allowable range based on the component classification information; and f) a result output unit configured to output the integration degree of coincidence and a decision additional information according to a judgement by the judgement unit and a result of the classification for a predetermined number of reference substances in descending order of the degree of integration degree of coincidence.

As the measurement result of the component included in the analysis target sample and the physical quantity corresponding to its content, for example, a semi-quantitative value (a pair of a contained element and its content ratio) obtained from a measurement result of an EDX and a pair of a position (wave number) and a size (absorption rate) of the absorption spectrum of an absorption peak obtained from a measurement result of an FTIR may be used.

In the sample analysis system according to embodiments of the present invention, a user designates one or more reference substances to be collated with an analysis target sample. Then, in the same manner as in the sample analysis system of the prior application, the measurement result of the target sample obtained by at least one of a fluorescent X-ray analyzer, an atomic absorption spectrophotometer, and an inductively coupled plasma emission analyzer and at least one of an infrared spectrophotometer and a Raman spectrophotometer is compared with the measurement result of the reference substance. With this, for each reference substance, the degree of coincidence is obtained for each analysis device.

Further, in the sample analysis system according to the present invention, the component commonality with the analysis target sample and the difference of the physical quantities of the respective components are obtained, and it is judged whether or not the difference is within an allowable range. Further, the components in which the physical quantity difference is outside the allowable range are classified based on the component classification information. Then, additional information corresponding to these results is output together with the integration degree of coincidence.

In the sample analysis system of the prior application, only the integration degree of coincidence was displayed. For this reason, when the integration degree of coincidence is low, the user was required to carefully investigate the measurement results of the analysis target sample and the measurement results of the reference substance in large quantity. This was a burden for a less skilled user. However, in the sample analysis system according to the present invention, additional information is output in addition to the integration degree of coincidence. For this reason, even when the degree of integration degree of coincidence is low, a less skilled user can make a judgment, such as "it is a reference substance A containing a lot of impurities", based on additional information.

The sample analysis system according to the present invention can be suitably used not only for analyzing foreign substances as described with respect to the prior art but also for, e.g., inspecting raw materials for manufacturing products at factories. In order to secure quality of products, it is preferable to always use a material of constant quality. However, in recent years, a so-called "silent change" in which suppliers change a part of ingredients of raw materials without prior notice due to difficulty in obtaining raw materials and a cost reduction has become a problem. Under such circumstances, when using the sample analysis system according to the present invention, it is only necessary to know the degree of coincidence (more specifically, suitability as raw materials) of the target sample (for example, a part collected from a raw material) and the standard item of raw materials. In this case, the user is required to specify only one reference substance. With this, the number of reference substances that the measurement result collation unit collates the measurement result can be reduced, reducing the calculation load, which in turn can obtain the result efficiently. Further, only the collation result of the reference substance specified by the user is output. Therefore, even in cases where there is a reference substance with a higher integration degree of coincidence than the reference substance to be compared, there is no worry that the user will misunderstand the reference substance to be compared. Of course, also in analyzing foreign substances, in cases where it is possible to narrow down the target in advance, the user can specify a small number of reference substances.

Further, in the case of using for an inspection of raw materials as described above, it is preferable to configure such that components other than components that characterize the reference substance (for example, components necessary for raw materials) are divided into components (base metals, substrates, etc.) in which the content do not affect the quality, etc., of the product and a component (impurities, etc.) in which the content affects the product quality, etc., and different additional information is output according to them. Furthermore, it is also possible to configure such that components classified as impurities are divided into prohibited impurities such as harmful components and other impurities (general impurities) and different additional information is output depending on them. Accordingly, it is possible to know the suitability, etc., as raw materials in more detail.

With the sample analysis system according to the disclosed embodiments, even when only reference substances with low integration degree of coincidence are presented, less skilled users can easily make judgments on the analysis target sample by referring to the additional information.

BRIEF DESCRIPTION OF THE DRAWINGS

FIG. 2 is an example of an EDX quantitative analysis data used in the sample analysis system of the present example.

FIG. 3 is an example of an FTIR quantitative analysis data used in the sample analysis system of the present example.

FIG. 7 is an example of a reference substance designation screen displayed in the sample analysis system of this example.

FIG. 8 is an example of an analysis screen displayed in the sample analysis system of this example.

FIGS. 9A and 9B show an example of a collation result of quantitative analysis data in this example.

FIG. 10 is an example of an analysis result screen displayed in the sample analysis system of this example.

FIG. 12 is another example of the analysis result screen displayed in the sample analysis system of this example.

EMBODIMENTS FOR CARRYING OUT THE INVENTION

An example of a sample analysis system according to the present invention will be described below with reference to the drawings. As described above, the present invention is an improvement of the sample analysis system of the prior application.

Figure 1:
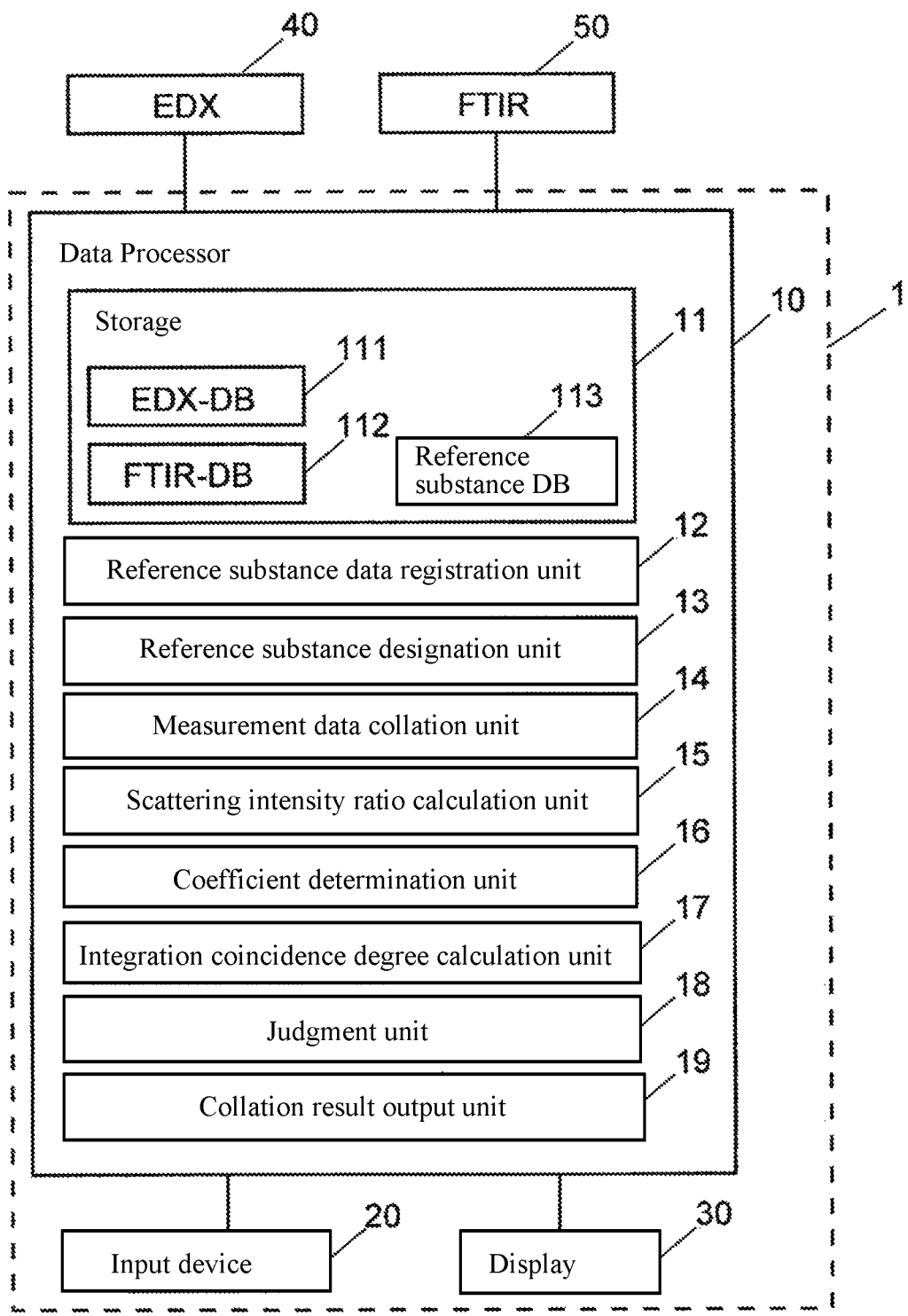
FIG. 1 is a configuration diagram of a main part of one example of a sample analysis system according to the present invention.

FIG. 1 shows a configuration of a main part of the sample analysis system of this example. The sample analysis system 1 of this example includes a data processor 10, an input device 20, and a display 30 connected to the data processor 10. In addition to storage 11, the data processor 10 is provided with, as functional blocks, a reference data registration unit 12, a reference substance designation unit 13, a measurement result collation unit 14, a scattering intensity ratio calculation unit 15, a coefficient determination unit 16, an integration coincidence degree calculation unit 17, a judgment unit 18, and a collation result output unit 19. The data processor 10 may be a computer. The computer may comprise a processor (e.g., a microprocessor, a controller, a CPU, a GPU, etc.) or processors configured by software or may be dedicated hardware or firmware (e.g., an electronic or optical circuit). A "computer" may be one or more apparatuses and/or one or more systems that are capable of accepting a structured input, processing the structured input according to prescribed rules, and producing results of the processing as output. Examples of a computer include: a stationary and/or portable computer; a computer having a single processor (e.g., a CPU), multiple processors, or multi-core processors; a general purpose computer; a supercomputer; a mainframe; a workstation; a server; a client; a tablet; and application-specific hardware, such as, for example, a digital signal processor (DSP) or a field-programmable gate array (FPGA). Each of the above functional blocks (e.g., units 12 through 19) may be embodied by executing a software, such as a sample analysis program by at least one processor (e.g., CPU). Each functional block (or unit) described herein may comprise a separate computer, or some or all of the functional block (or unit) may be comprised of and share the hardware of the same computer. Connections and interactions between the functional block (or unit) may be hardwired and/or in the form of data (e.g., as data stored in and retrieved from memory of the computer, such as a register, buffer, cache, storage drive, etc., such as part of an application programming interface (API)). Each functional block (or unit) may correspond to separate segment or segments of software (e.g., a subroutine) which configure the computer, or may correspond to segment(s) of software that also correspond to one or more other functional block (or unit). As is understood, "software" refers to prescribed rules to operate a computer, such as code or script. Storage 11 may comprise conventional memory of a computer, such as a hard drive (which may be a solid state drive, DRAM, NAND flash memory, etc.). Input device 20 may comprise conventional computer input devices, such as a keyboard, mouse, trackpad, touchscreen (of display 30), etc. In storage 11, an energy dispersive X-ray fluorescence analysis database (EDX-DB) 111, a Fourier transform infrared spectroscopic database (FTIR-DB) 112, and a reference substance database (reference substance DB) 113 are stored and maintained. Furthermore, in storage 11, information on an allowable range and additional information, which will be described later, are also stored. Further, the data processor 10 is connected to the fluorescent X-ray analyzer (EDX) 40 and the Fourier transform infrared spectrophotometer (FTIR) 50. The data obtained by measuring samples using these devices can be stored in storage 11.

In an EDX-DB 111, the measurement data obtained by measuring a plurality of reference substances with the EDX 40 (or another EDX) is stored. The measurement data on the EDX includes an ID number for identifying a reference substance, a name of the reference substance, an image obtained by capturing an image of an X-ray irradiation site with a camera mounted on the apparatus, a measurement condition, a profile (EDX spectrum data), and quantitative analysis data obtained from the profile. In addition, comments on reference substances (e.g., the measurement site of the reference substance) created by a measurer or the like are also included.

FIG. 2 shows an example of quantitative analysis data of the EDX. In the quantitative analysis data of the EDX, in addition to the content (weight percent) which is a semi-quantitative value of each component (element) obtained from the measurement data obtained by the EDX 40 (or another EDX), component classification information of each component (element) contained in the reference substance is included. The component classification information is information attached by a measurer of the reference substance or a person who is familiar with the characteristics of the reference substance, and is information that classifies each component (element) contained in the reference substance into a component required for the reference substance (a component that characterizes the reference substance), a component in which the content does not affect characteristics (quality, etc.), and components other than the above (impurities). In the example shown in FIG. 2, check boxes are provided for components that are necessary for the reference substance and components in which the content does not affect. The components in which none of the check boxes are checked are classified as impurities.

In the FTIR-DB 112, measurement data obtained by measuring a plurality of reference substances with the FTIR 50 (or another FTIR) is stored. The measurement data on the FTIR includes an ID number for identifying a reference substance, a name of a reference substance, a measurement condition, spectral data, and quantitative analysis data obtained from the spectral data. It also contains comments on reference substances created by experts, etc.

FIG. 3 shows an example of quantitative analysis data of the FTIR. In the quantitative analysis data of the FTIR, in addition to the position of the absorption peak (wave number unit) obtained from the measurement data obtained by the FTIR 50 (or another FTIR) and the absorption rate at that position, component classification information of the wave number corresponding to the position is included. Although a specific name of a component is not described in FIG. 3, a position of an absorption peak in an absorption spectrum is unique to a component. For this reason, the position (wave number) can be regarded as information corresponding to one component. The component classification information is information to be attached by a measurer of the reference substance or a person who is familiar with the characteristics of the reference substance, and is information for classifying each component contained in the reference substance into a component necessary for the reference substance (component characterizing the reference substance), a component whose content does not affect characteristics (quality, etc.), and other components (impurities). Also in the example shown in FIG. 3, check boxes are provided for components that are necessary for the reference substance and components that do not affect the content. Components that are not checked are classified as impurities. In the FTIR quantitative analysis data, an absorption rate is used instead of the quantitative value in the EDX quantitative analysis data. The value of the absorption rate is standardized so that the maximum value becomes 1.0.

In the reference substance DB 113, data related to a plurality of reference substances themselves are stored. Specifically, the ID number identifying the reference substance, the name of the reference substance, the elements and compounds contained in the reference substance and its content (or its content ratio), the photograph (camera image) of the reference substance, the obtained date and time or place of the reference substance, etc., are included.

Figure 4:
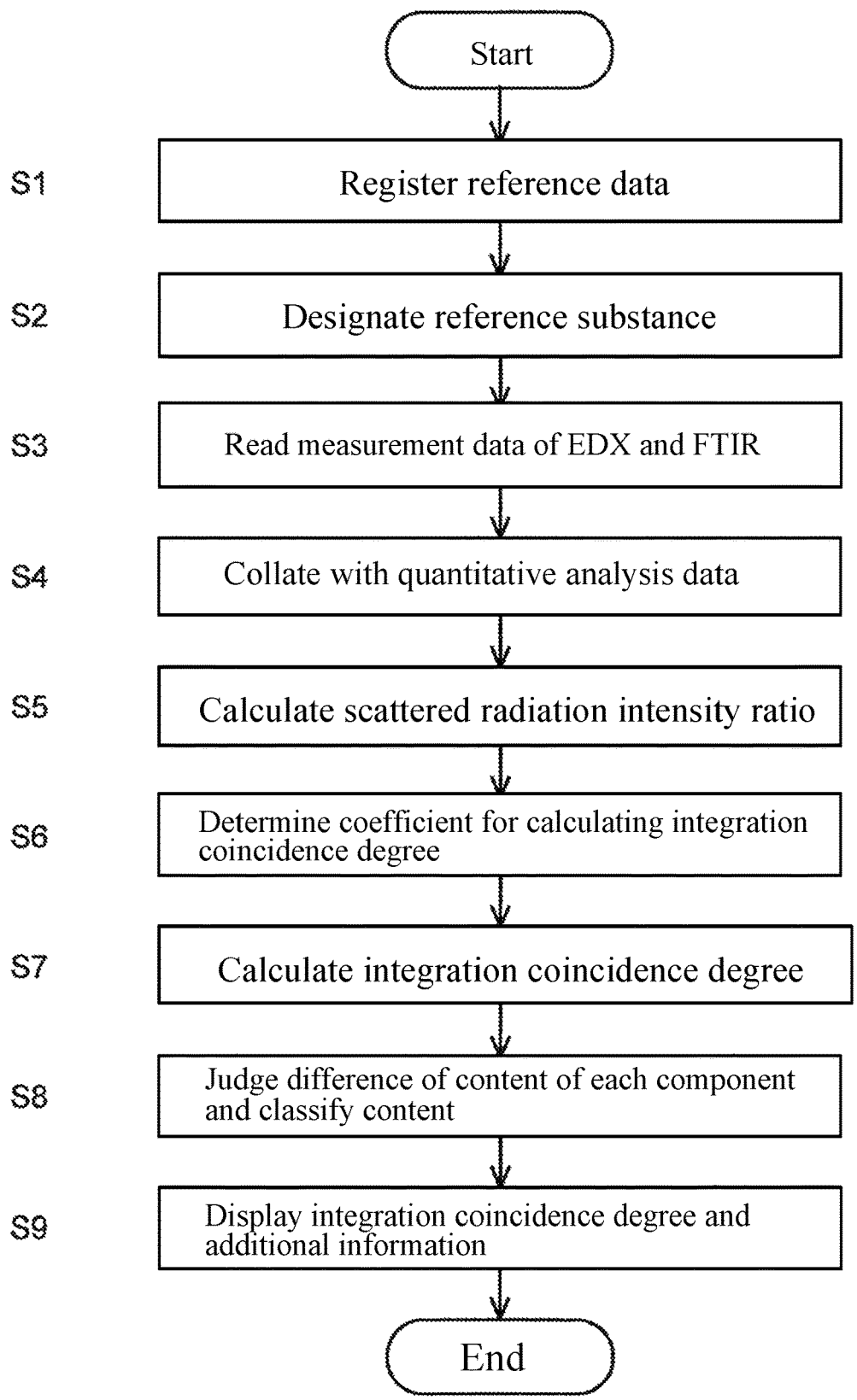
FIG. 4 is a flowchart of an analysis using the sample analysis system of the present example.

Next, a specific analysis procedure using the sample analysis system 1 of this example will be described. Here, as an example, a case in which quality is evaluated by comparing a bottom plate B (analysis target sample) which is a material provided by a supplier in a factory, etc., with a reference product of the material (bottom plate B) will be explained with reference to the flowchart of FIG. 4.

Figures 5, 6:
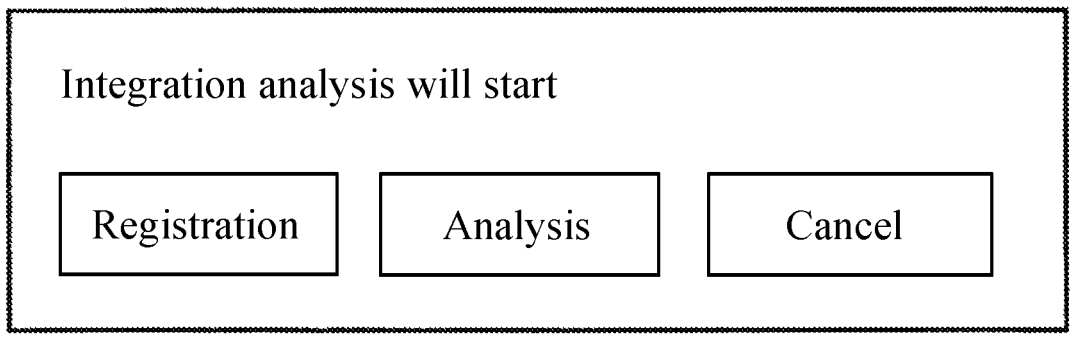
FIG. 5 is an example of an initial screen displayed in the sample analysis system of this example.
FIG. 6 is an example of a library used in the sample analysis system of this example.

When a user operates a sample analysis program stored in the sample analysis system of this example, as shown in FIG. 5, three options, "Registration", "Analysis", and "Cancel", are displayed on the display 30. When the user selects "Registration" through the input device 20, the reference data registration unit 12 displays a library of reference substance data on the display 30 (FIG. 6). When a new registration button 72 is pushed on this screen, the screen shifts to a screen for allowing the user to input (specify the file, etc.) measurement data of the EDX and the FTIR of the reference substance to be newly registered and data related to the reference substance itself. When the user inputs them, the reference data registration unit 12 registers the data of the input reference substance in the EDX-DB111 and the FTIR-DB112, and in the reference substance DB113 (Step S1). Then, the screen returns to the screen of FIG. 5. Once data of a reference item of a reference substance is registered, there is no need to register the data of the same reference substance thereafter (it is not necessary to perform Step S1). Other functions on the library screen will be described later.

After registering the reference substance data, the screen returns to the screen shown in FIG. 5. When a user selects "Analysis" with the input device 20, the reference substance designation unit 13 makes the display 30 display the reference substance designation screen as shown in FIG. 7. When the user selects one of the reference substances on this screen and then selects (presses a touchscreen of the display or clicks with a mouse or trackpad input) the "View" button, the measurement data of the selected reference substance is read from the EDX-DB111 and the FTIR-DB112 and displayed on the screen. When the "Details" button is pressed, the information of the selected reference substance is read from the reference substance DB113 and displayed on the screen. When the user selects the reference substance and then presses the "Analysis" button, it proceeds to the analysis of the analysis target sample. In this example, only the "Bottom board B" is selected, but a plurality of reference substances may be selected.

When the user selects the "Analysis" on the screen shown in FIG. 7, the reference substance designation unit 13 displays, as an analysis screen, four options, "EDX", "FTIR", "Integration", and "Cancel", on the display 30 as shown in FIG. 8. When the "EDX" is selected, the analysis of the analysis target sample based only on the energy dispersive X-ray analysis data (EDX data) is started. When the "FTIR" is selected, the analysis of the analysis target sample based on only the Fourier transform infrared spectroscopic data (FTIR data) is started. When the "Integration" is selected, the analysis of the analysis target sample based on both the EDX data and the FTIR data is started. When the "Cancel" is selected, it returns to the screen of FIG. 5.

Hereinafter, a case in which a user selects the "Integration" will be described. When a user selects the "Integration", the measurement result collation unit 14 makes the display 30 display a screen for allowing the user to specify the analysis target samples of the EDX and FTIR measurement data. When the user specifies the measurement data of the EDX and the measurement data of the FTIR stored in storage 11, respectively, the quantitative analysis data (quantitative value of each element) of the analysis target sample is read out from the EDX measurement data, and the quantitative analysis data (wave number and absorption rate) is read out from the FTIR measurement data (Step S3). In this example, the quantitative analysis data of the measurement target sample preliminarily stored is read out, but it may be configured such that the EDX measurement and the FTIR measurement of the analysis target sample are performed in Step S3 to obtain quantitative analysis data from each of them.

Subsequently, the measurement result collation unit 14 determines, on respective quantitative analysis data of EDX and quantitative analysis data of FTIR, whether the analysis target sample and the reference substance have common components (component commonality) and obtains the difference of contents of each composition (Step S4). FIG. 9A shows an example of EDX quantitative analysis data, and FIG. 9B shows an example of FTIR quantitative analysis data.

The measurement result collation unit 14 also obtains the degree of coincidence of the EDX quantitative analysis data and the FTIR quantitative analysis data. The degree of coincidence of the EDX quantitative analysis data may be a value obtained by, for example, for each element, obtaining the sum (difference degree) of absolute values of the difference between the quantitative value of each element contained in the analysis target sample and the quantitative value of each element contained in the reference substance and subtracting the sum from a predetermined value. In many cases, as the quantitative value of the analysis target sample or the reference substance, a quantitative value (semi-quantitative value) of each element obtained by an FP method in which the composition of the main component of the analysis target sample (or reference substance) is assumed and measured intensity of a fluorescent X-ray is reproduced using a theoretical formula is used. Of course, a quantitative value obtained by a calibration curve method may be used. Further, the degree of coincidence of FTIR quantitative analysis data of may be a value obtained by, for example, obtaining the sum of absolute values (difference degree) of the difference of absorption rate in each wave number after standardizing the maximum absorption rate of the analysis target sample and the maximum absorption rate of the reference substance to 1.0, respectively, and subtracting the sum from a predetermined value.

For each of the EDX quantitative analysis data and the FTIR quantitative analysis data, after collating the analysis target sample and the reference substance, the scattering intensity ratio calculation unit 15 reads the measurement condition and the profile (the spectrum obtained at the time of measurement) from the EDX data file. Then, based on the energy of the irradiation X-ray at the time of measurement, the intensity of the Compton scattered radiation (peak at the energy position different from the irradiation X ray) and the intensity of the Rayleigh scattered radiation (peak at the same energy position as the irradiation X ray) are obtained, and the ratio (the intensity of the Compton scattered irradiation/the intensity of the Rayleigh scattered radiation) is obtained (Step S5).

Subsequently, the coefficient determination unit 16 determines weighting coefficients (EDX coefficient and FTIR coefficient) for EDX data and FTIR data based on the ratio (the intensity of the Compton scattered radiation/the intensity of the Rayleigh scattered radiation) (Step S6). Specifically, when the ratio is 1.00 or less, it is determined that the analysis target sample is an inorganic substance, and the EDX coefficient and the FTIR coefficient are determined to be 0.8 and 0.2, respectively. Also, when the ratio is greater than 1.00 and not greater than 2.00, it is determined that the analysis target sample is a mixture of an organic substance and an inorganic substance, and both the EDX coefficient and the FTIR coefficient are determined to be 0.5. Further, when the ratio is larger than 2.00, it is determined that the analysis target sample is an organic substance, and the EDX coefficient and the FTIR coefficient are determined to be 0.2 and 0.8, respectively. In this example, the number of combination of the EDX coefficient and the FTIR coefficient is set to three, but it may be divided in more detail, or the EDX coefficient and the FTIR coefficient may be determined by using an equation in which the aforementioned ratio is a variable.

When the EDX coefficient and the FTIR coefficient are obtained by the coefficient determination unit 16, the integration coincidence degree calculation unit 17 calculates the integration degree of coincidence by multiplying the degree of coincidence of the EDX quantitative analysis data obtained for the reference substance by the EDX coefficient, multiplying the degree of coincidence of the FTIR quantitative analysis data by the FTIR coefficient, and obtaining the sum of them (Step S7).

When the integration degree of coincidence is determined, the judgment unit 18 determines, for each of the EDX quantitative analysis data and the FTIR quantitative analysis data, whether or not the difference of the content of each component (element) is within a predetermined allowable range stored in storage 11. Also, based on the component classification information described with reference to FIGS. 2 and 3, the component (element) whose difference is outside the allowable range is classified into one of a necessary component, a component causing no influence, and impurities (Step S8). In this example, the allowable range for the EDX quantitative analysis data is set to ±20% of the content of the reference substance, and the allowable range for the FTIR quantitative analysis data is set such that the difference of the absorption rate is ±0.10. These values may be arbitrarily determined according to the characteristics of the analysis target sample. Further, allowable ranges different every component (element) may be set.

In the EDX quantitative analysis data of FIG. 9A, only Ca is outside the allowable range, and the element Ca is classified as a required component. Further, in the FTIR quantitative analysis data of FIG. 9B, only the absorption rate of wave number of 872 cm$^{-1}$ is outside the allowable range, which is classified as an impurity.

Finally, the collation result output unit 19 displays the analysis result of the analysis target sample on the display 30 (Step S9). An example is shown in FIG. 10. In addition to the integration degree of coincidence, the collation result output unit 19 reads out additional information corresponding to the component determined to be outside the allowable range by the judgment unit 18 from storage 11 and displays it on the display 30. Specifically, based on the fact that the element Ca which was decided to be outside the allowable range in the EDX quantitative analysis data is classified as a required component (element), additional information "Necessary component (Ca) is insufficient" is displayed as additional information. Further, based on the fact that the component (wave number 872 cm$^{-1}$) which was decided to be outside the allowable range in the FTIR quantitative analysis is classified as an impurity, additional information "Large amount of impurities (wavenumber 872 cm$^{-1}$) is contained" is displayed as additional information. Further, in cases where a component which is outside the allowable range is a component causing no influence, additional information "there exists a component (component name) causing no influence, but there is no problem in quality".

Here, only the integration analysis has been described. However, in an analysis using only the EDX and an analysis using only the FTIR, the analysis is performed by the same procedure as described above (except Steps S5 to S7).

In the sample analysis system of this example, in the same manner as in the sample analysis system of the previous application, based on the intensity ratio of the Compton scattered radiation and the Rayleigh scattered radiation, it is judged whether or not the analysis target sample is one of an inorganic substance, an organic substance, and a mixture thereof. When it is an inorganic substance, the integration degree of coincidence is calculated by using a coefficient that weights the EDX measurement data suitable for analyzing inorganic substances. When it is an inorganic substance, the integration degree of coincidence is calculated by using a coefficient that weights the FTIR measurement data suitable for analyzing organic substances. Therefore, the integration degree of coincidence can be appropriately obtained depending on the characteristics of the analysis target sample.

Further, in the sample analysis system of this example, not only the integration degree of coincidence of the analysis target sample and the reference substance but also additional information are displayed. For this reason, even when the degree of integration degree of coincidence is low, a less skilled user can easily make judgments on the quality and suitability of the analysis target sample. Further, only the collation result of the reference substance specified by the user is output. Therefore, even in cases where there is a reference substance with a higher degree of integration degree of coincidence than the reference substance to be compared, there is no worry that the user will misunderstand the reference substance to be compared.

Figure 11:
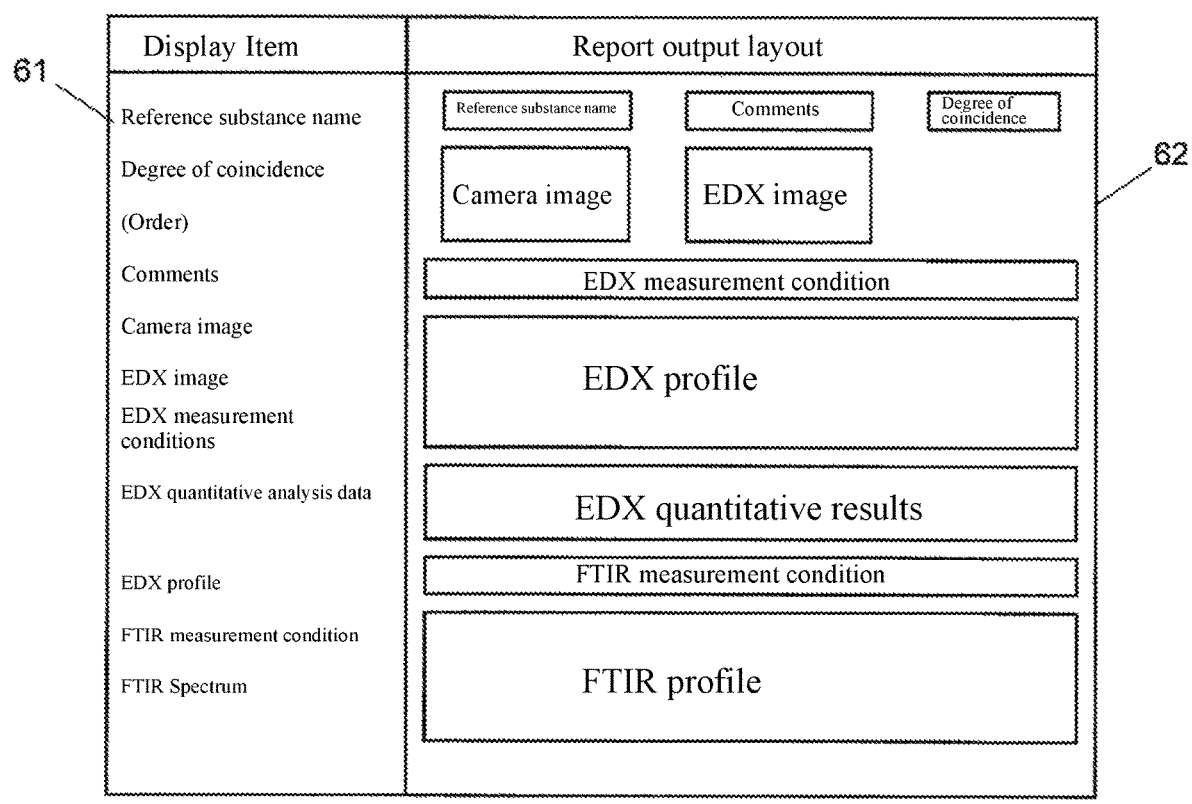
FIG. 11 is an example of a screen for editing a report output layout in the sample analysis system of this example.

Hereinafter, an additional configuration provided in the sample analysis system of this example will be described. In the sample analysis system of this example, the analysis result of the analysis target sample obtained as described above can be printed as a report. FIG. 11 shows an example of a screen for setting items and layouts of reports to be printed. In the display item column 61 on the left side of the screen, items that can be displayed in the report are listed. Items that can be displayed in the report include a reference substance name, the degree of coincidence of an analysis target sample and a reference substance, comments on the reference substance (information on the acquisition date and time of the substance, the date and time of the measurement, etc.), a camera image, an EDX image, an EDX measurement condition, an EDX quantitative analysis data, an EDX profile, an FTIR measure condition, and an FTIR spectrum. When a user selects a plurality of reference substances in Step S2, the order of degree of coincidence is also displayed.

When a user drags and drops one of these items to the layout editing area 62 on the right side of the screen, the area for displaying the item is shown in the layout column. The output layout of the report is determined by appropriately adjusting the position and size of the area displayed in the layout column. At this time, when an EDX profile or an FTIR spectrum is selected, the EDX profile and the FTIR spectrum of the analysis target sample or the reference substance are superimposed and displayed in different colors. Thus, the user can check the degree of coincide of the measurement data of the analysis target sample and the reference substance on the report.

Next, functions relating to the library of FIG. 6 will be described. In the library 71 displayed on the screen of FIG. 6, as described above, it is possible not only to additionally register measurement data of a reference substance but also to confirm whether information and measurement data regarding the reference substance is stored in storage 11. For each item, when the measurement data of the reference substance, etc., is stored, a check mark is displayed, and when it is not saved, it is displayed as "Unregistered". When a plurality of camera images is registered, the number of the camera images is displayed together with a check mark.

When a user selects an unregistered item in the library 71, a screen for designating a file such as measurement data is displayed. When the user designates a file, the file is registered in the database. When an item marked with a checkmark is selected, it is possible to confirm the contents already registered in database or edit comments. Further, when the new registration button 72 is selected, the screen shifts to a screen for additionally registering measurement data, etc., of a new reference substance in the database. It is also possible to search the reference substance registered in the database through the box displayed in the lower part of the screen and the search button 73.

In the sample analysis system of this example, measurement data (e.g., electron microscope image) other than the EDX data and the FTIR data to be used for analyzing an analysis target sample and report information outputted in the past can be saved in storage 11, and also can be managed in association with the EDX data, the FTIR data, etc., via a reference substance ID. With this, measurement data of reference substances acquired for various purposes can be unitarily managed by the sample analysis system of this example.

The above-described example is merely an example and can be appropriately changed in accordance with the spirit of the present invention. In the aforementioned example, a case in which a raw material is inspected at a factory or the like is described as an example, but the present invention can also be used for, e.g., specifying foreign substances. In this case, since foreign substances are unknown, the aforementioned steps are performed for all reference substances stored in the library (that is, in Step S2, all reference substances are designated). In this case, in order to reduce the load on the process of the sample analysis system 1, it may be configured such that a predetermined number of reference substances having a high degree of coincidence is extracted as a primary candidate reference substance, and only for the primary candidate references and the integration degree of coincidence or the like is obtained. Alternatively, it may be configured such that a predetermined number of reference substances having a high degree of integration degree of coincidence is extracted as a secondary candidate reference object and only the secondary candidate reference objects are processed by the judgment unit 18. An example of an analysis result display screen obtained in this case is shown in FIG. 12. In FIG. 12, five reference substances are displayed in ascending order of integration degree of coincidence, and additional information on each is displayed in a simplified manner. The upward arrow indicates that the content of the component (element) contained in the foreign substance is larger than the allowable range, and the downward arrow indicates that the content of the component (element) contained in the foreign substance is smaller than the allowable range. As for impurities, only the component (element) name is displayed. Further, by selecting the column of the reference substance name, the same screen as shown in FIG. 10 can be displayed for each reference substance.

In the aforementioned example, components are classified into three types, i.e., a required component, a component causing no influence, and impurities, but the impurities may be further classified into prohibited impurities such as harmful components and general impurities other than the prohibited impurities. In this case, it is preferably configured such that the allowable range of the prohibited components is set to 0 and additional information is always output in cases where the prohibited components are included. With this, it is possible to know the suitability, etc., as raw materials in more detail.

In the aforementioned example, it is configured such that the database is provided in storage 11 of the data processor 10. However, each database may be provided in another device connected to the data processor 10, or it may be configured to provide an online database to which the data processor 10 can be connected via a network.

In the aforementioned example, the EDX 40 and the FTIR 50 are connected to the sample analysis system 1, but they are not always required to be connected the sample analysis system 1. As an analysis device suitable for analyzing inorganic substances, other than an EDX, there are an atomic absorption spectrophotometer and an inductively coupled plasma emission analyzer. When using these devices, the measurement data of the analysis target sample obtained by using these devices may be used in place of or in addition to the EDX data. Furthermore, it may be configured to use a Raman spectrophotometer as an analysis device suitable for analyzing organic substances in the same manner as in the aforementioned example.

DESCRIPTION OF REFERENCE SYMBOLS

1: sample analysis system
10: data processor
  11: storage
    111: EDX-DB
    112: FTIR-DB
    113: reference substance DB
  12: reference data registration unit
  13: reference substance designation unit
  14: measurement result collation unit
  15: scattering intensity ratio calculation unit
  16: coefficient judgment unit
  17: integration coincidence degree calculation unit
  18: judgment unit
  19: collation result output unit
20: input device
30: display
40: EDX
50: FTIR
61: display item column
62: layout editing area
71: library list
72: new registration button
73: search button

The invention claimed is:

1. A sample analysis system used for analyzing an analysis target sample from measurement results of components contained in the analysis target sample and physical quantities corresponding to contents of the components obtained by a measurement by each of a plurality of analysis devices including at least one of a fluorescent X-ray analyzer, an atomic absorption spectrophotometer, and an inductively coupled plasma emission analyzer and at least one of an infrared spectrophotometer and a Raman spectrophotometer, the sample analysis system comprising:
  a) a reference substance database in which information on a plurality of reference substances is amassed, wherein the information on each reference substance includes measurement results of a plurality of components contained in the reference substance and the physical quantities measured by each of the plurality of analysis devices and component classification information indicating whether or not each of the plurality of components characterizes the reference substance;
  b) a reference substance designation unit configured to allow a user to designate one or more reference substances from among the plurality of reference substances to be collated with the analysis target sample;
  c) a measurement result collation unit configured to, for each of the one or more reference substances and for each analysis device, collate a measurement result of the reference substance with a measurement result of the analysis target sample, and obtain a commonality of components indicating whether or not common components exist, a difference between the physical quantities of each component, and a degree of coincidence of the measurement results;
  d) an integration coincidence degree calculation unit configured to obtain an integration degree of coincidence in which the degrees of coincidence obtained by respective analysis devices are integrated for each of the one or more reference substances,
  e) a judgment unit configured to, for each of the one or more reference substances, judge whether or not the difference between the physical quantities of each component is within a predetermined allowable range and classify a component in which the difference between the physical quantities is outside the predetermined allowable range based on the component classification information; and
  f) a result output unit configured to output the integration degree of coincidence and additional information according to a judgement by the judgement unit and a result of the classification for a predetermined number of reference substances in descending order of the integration degree of coincidence,
wherein the plurality of analysis devices includes a fluorescent X-ray analyzer, and
wherein the sample analysis system further comprises:
  g) a scattered radiation intensity ratio calculation unit configured to obtain an intensity ratio of Compton scattered radiation and Rayleigh scattered radiation from measurement data of the target sample using the fluorescent X-ray analyzer; and
  h) a coefficient determination unit configured to determine a coefficient that gives weighting to the degree of coincidence on the fluorescent X-ray analyzer, the infrared spectrophotometer, or the Raman spectrophotometer, based on the intensity ratio,
wherein the integration coincidence degree calculation unit calculates the integration degree of coincidence by reflecting the coefficient in the degree of coincidence on the fluorescent X-ray analyzer, the infrared spectrophotometer, or the Raman spectrophotometer.

2. The sample analysis system as recited in claim 1,
wherein the component classification information is information for classifying the plurality of components into one of a component that characterizes the reference substance, a component that does not cause a problem due to the content, and an impurity component.

3. The sample analysis system as recited in claim 2,
wherein the impurity component is further classified into a general impurity and a prohibited impurity.

4. The sample analysis system as recited in claim 2,
wherein the plurality of analysis devices includes a fluorescent X-ray analyzer, and
wherein the sample analysis system further comprises:
  g) a scattered radiation intensity ratio calculation unit configured to obtain an intensity ratio of Compton scattered radiation and Rayleigh scattered radiation from measurement data of the target sample using the fluorescent X-ray analyzer; and
  h) a coefficient determination unit configured to determine a coefficient that gives weighting to the degree of coincidence on the fluorescent X-ray analyzer, the infrared spectrophotometer, or the Raman spectrophotometer, based on the intensity ratio,
wherein the integration coincidence degree calculation unit calculates the integration degree of coincidence by reflecting the coefficient in the degree of coincidence on the fluorescent X-ray analyzer, the infrared spectrophotometer, or the Raman spectrophotometer.

5. The sample analysis system as recited in claim 3,
wherein the plurality of analysis devices includes a fluorescent X-ray analyzer, and
wherein the sample analysis system further comprises:
  g) a scattered radiation intensity ratio calculation unit configured to obtain an intensity ratio of Compton scattered radiation and Rayleigh scattered radiation from measurement data of the target sample using the fluorescent X-ray analyzer; and
  h) a coefficient determination unit configured to determine a coefficient that gives weighting to the degree of coincidence on the fluorescent X-ray analyzer, the infrared spectrophotometer, or the Raman spectrophotometer, based on the intensity ratio,
wherein the integration coincidence degree calculation unit calculates the integration degree of coincidence by reflecting the coefficient in the degree of coincidence on the fluorescent X-ray analyzer, the infrared spectrophotometer, or the Raman spectrophotometer.

* * * * *